US011984203B1

(12) United States Patent
Uribe et al.

(10) Patent No.: US 11,984,203 B1
(45) Date of Patent: May 14, 2024

(54) SYSTEM AND PROCESSES FOR ANONYMOUS DNA/RNA BIOSPECIMEN TRACKING FOR HUMAN FAMILIES USING FILTERS AND NON-FUNGIBLE-TOKENS

(71) Applicants: Daniel Francisco Uribe, San Mateo, CA (US); William Buchanan, San Mateo, CA (US)

(72) Inventors: Daniel Francisco Uribe, San Mateo, CA (US); William Buchanan, San Mateo, CA (US)

( * ) Notice: Subject to any disclaimer, the term of this patent is extended or adjusted under 35 U.S.C. 154(b) by 405 days.

(21) Appl. No.: 17/151,114

(22) Filed: Jan. 15, 2021

Related U.S. Application Data (60) Provisional application No. 62/936,166, filed on Nov. 15, 2019.

(51) Int. Cl.

| | |
|---|---|
| *G16H 10/40* | (2018.01) |
| *G06F 16/23* | (2019.01) |
| *G06F 21/62* | (2013.01) |
| *G06Q 20/36* | (2012.01) |
| *G06Q 50/28* | (2012.01) |
| *G16B 10/00* | (2019.01) |
| *G16H 10/65* | (2018.01) |
| *G16H 40/20* | (2018.01) |
| *H04L 9/32* | (2006.01) |

(52) U.S. Cl.
CPC ........ *G16H 10/40* (2018.01); *G06F 16/2379* (2019.01); *G06F 21/6254* (2013.01); *G06Q 20/363* (2013.01); *G06Q 50/28* (2013.01); *G16B 10/00* (2019.02); *G16H 10/65* (2018.01); *G16H 40/20* (2018.01); *H04L 9/3213* (2013.01)

(58) Field of Classification Search
CPC ........ G16H 10/40; G16H 40/20; G16H 10/65; G06F 16/2379; G06F 21/6254; G06Q 20/363; G06Q 50/28; G16B 10/00; H04L 9/3213

See application file for complete search history.

(56) References Cited

U.S. PATENT DOCUMENTS

| | | | |
|---|---|---|---|
| 2017/0053908 A1* | 2/2017 | Hoffman | H01L 29/1606 |
| 2018/0330052 A1* | 11/2018 | Barrus | G06F 21/6254 |
| 2019/0237162 A1* | 8/2019 | Ye | G16B 20/00 |
| 2020/0076798 A1* | 3/2020 | Lidsky | H04L 63/083 |

* cited by examiner

*Primary Examiner* — Gregory D. Moseley
(74) *Attorney, Agent, or Firm* — Plager Schack LLP; Mark H. Plager; Stephen Hallberg (57) ABSTRACT

Anonymous DNA/RNA biospecimen tracking process is disclosed for human families to use an anonymous DNA/RNA biospecimen extraction kit that utilizes public key infrastructure, asymmetric encryption, and Non-Fungible-Tokens from a public Blockchain or Distributed Ledger Technology distributed ledger/blockchain to create a Self-Sovereign DNA Fingerprint for each DNA donor, relate, claim ownership, consent to use, establish biological relationship between donors, and keep track of corresponding multi-omics data sets. The process allows entire families to create a Self-Sovereign DNA Fingerprint for each member/donor (using at least 50 SNPs) and explore the genomic revolution without risking their identities, losing track of their biosamples, corresponding datasets and customize data governance by using individual or multi signature wallets in which all data is encrypted using a unique master family encryption key.

6 Claims, 7 Drawing Sheets

SYSTEM AND PROCESSES FOR ANONYMOUS DNA/RNA BIOSPECIMEN TRACKING FOR HUMAN FAMILIES USING FILTERS AND NON-FUNGIBLE-TOKENS

CLAIM OF BENEFIT TO PRIOR APPLICATION

This application claims benefit to U.S. Provisional Patent Application 62/936,166, entitled "ANONYMOUS DNA/RNA BIOSPECIMEN TRACKING PROCESS FOR HUMAN FAMILIES TO USE AN ANONYMOUS DNA/RNA BIOSPECIMEN EXTRACTION KIT THAT UTILIZES PUBLIC KEY INFRASTRUCTURE (PKI), ASYMMETRIC ENCRYPTION, NON-FUNGIBLE-TOKENS (NFT) ON A PUBLIC BLOCKCHAIN TO CREATE A SELF-SOVEREIGN DIGITAL DNA FINGERPRINT FOR EACH DNA DONOR, RELATE, CLAIM OWNERSHIP, CONSENT TO USE, ESTABLISH BIOLOGICAL RELATIONSHIP BETWEEN DONORS, AND KEEP TRACK OF CORRESPONDING MULTI-OMICS DATA SETS," filed Nov. 15, 2019. The U.S. Provisional Patent Application 62/936,166 is incorporated herein by reference.

BACKGROUND

Embodiments of the invention described in this specification relate generally to biosample collection, tracking, and privacy, and more particularly, to a system and processes for anonymous DNA/RNA biospecimen tracking for human families using filters and non-fungible-tokens.

Current technology needs to share the data with a data broker that aggregates personal data to the DNA/RNA datasets, which is a point of privacy concern due to the most recent data breaches and conflicts of interests with the data broker's business model that needs to sell users data to big pharmaceutical companies to be sustainable.

Therefore, what is needed is a way to enable families (biological mother, father, and child or children) to sequence or genotype their DNA/RNA for different purposes (genomic medicine, human identification, creating a self-sovereign digital DNA fingerprint for each DNA donor, proof of genetic/biological relationship, nutrigenomics, pharmacogenomics profile, etc.) with privacy and customizable governance of the data sets from the minors, with customizable data governance that requires individual digital signature or multi-signature if custody is shared among the parents or guardians of the minors, as well as a way to perform anonymous DNA/RNA biospecimen tracking for human families using filters and non-fungible-tokens.

BRIEF DESCRIPTION

A novel anonymous DNA/RNA donor family biospecimen tracking system and novel anonymous DNA/RNA donor family biospecimen tracking processes are disclosed for human families using filters and non-fungible-tokens. In some embodiments, the anonymous DNA/RNA donor family biospecimen tracking system utilizes a bloom filter for members of human families to anonymously search databases and entities for indications of their anonymous DNA/RNA biospecimen being used.

In some embodiments, the anonymous DNA/RNA donor family biospecimen tracking processes include (i) an anonymous DNA/RNA donor family biospecimen preparation and ownership claiming process for human families of related donors to use an anonymous DNA/RNA biospecimen extraction kit that utilizes public key infrastructure (PKI), asymmetric encryption, and Non-Fungible-Tokens (NFT) on a public blockchain to create a self-sovereign digital DNA fingerprint for each DNA donor, relate, claim ownership, consent to use, establish biological relationship between donors, and keep track of corresponding multi-omics data sets associated with each donor biospecimen from provided in the anonymous DNA/RNA biospecimen extraction kit in some embodiments and (ii) a particular anonymous DNA/RNA biospecimen tracking process that utilizes a bloom filter for members of human families to anonymously search databases and entities for indications of their anonymous DNA/RNA biospecimen being used.

In some embodiments, the anonymous DNA/RNA donor family biospecimen preparation and ownership claiming process for human families of related donors to use an anonymous DNA/RNA biospecimen extraction kit that utilizes PKI, asymmetric encryption, and NFTs on a public blockchain to create a self-sovereign digital DNA fingerprint for each DNA donor, relate, claim ownership, consent to use, establish biological relationship between donors, and keep track of corresponding multi-omics data sets. The blockchain comprises one of a public blockchain and a distributed ledger technology blockchain. In some embodiments, the anonymous DNA/RNA donor family biospecimen preparation and ownership claiming process allows a person in the family to customize data governance by using individual or multi-signature wallets. In the end, all data is encrypted using a unique family encryption key. In some embodiments, the anonymous DNA/RNA donor family biospecimen preparation and ownership claiming process allows each member of an entire family (e.g., mother, father, children) to create a self-sovereign DNA fingerprint, using at least fifty genotyped single-nucleotide polymorphisms (SNPs), and explore the genomic revolution without risking their identities, losing track of their biosamples, corresponding datasets and customize data governance by using individual or multi signature wallets in which all data is encrypted using a unique master family encryption key. In some embodiments, the anonymous DNA/RNA donor family biospecimen preparation and ownership claiming process provides genetic/biological relationship verification that demonstrates and proves genetic familial link(s) between parent(s) and child(ren). For example, a child that is separated from one parent or both parents at a border crossing between two countries can be reunited by genetic proof linking the family together biologically/genetically. In this way, the anonymous DNA/RNA donor family biospecimen preparation and ownership claiming process results in potential minor child identification verification via familial DNA, such as from the child's biological mother and biological father. In some embodiments, the anonymous DNA/RNA donor family biospecimen preparation and ownership claiming process enhances biomedical/genetic analysis of DNA/RNA for identification of genetic mutation(s) between generations of genetically related individuals while still maintaining complete privacy of the identities of those individuals, yet ensuring that genetic/biomedical researcher or counselor knows that samples being analyzed/reviewed for mutation are genetically linked family members. In this way, tracing familial DNA mutations is made possible by the anonymous DNA/RNA biospecimen preparation and ownership claiming process because a researcher or a counselor interested in familial mutations can be assured that the biospecimen samples being analyzed/reviewed for mutation(s) are genetically linked family members (e.g., mother-child, father-child, etc.).

In some embodiments, the anonymous DNA/RNA donor family biospecimen preparation and ownership claiming process comprises (i) buying an anonymous DNA/RNA biospecimen extraction kit comprising at least three biosample collection tubes, (ii) creating a shared digital family wallet for at least three members of a family whose biosamples are to be collected in the biosample collection tubes of the anonymous DNA/RNA biospecimen extraction kit, (iii) registering the anonymous DNA/RNA biospecimen extraction kit under the shared family digital wallet, (iv) configuring a data governance scheme that requires at least one of an individual family member signature or multiple family member signatures, (v) collecting biosamples in the biosample collection tubes as provided by the members of the family, (vi) providing the anonymous DNA/RNA biospecimen extraction kit including the collected biosamples in the biosample collection tubes for delivery to an authorized lab via one of sending the anonymous DNA/RNA biospecimen extraction kit and depositing the anonymous DNA/RNA biospecimen extraction kit into an available locker slot of a local anonymous DNA/RNA biospecimen extraction kit vending machine, (vii) processing the biosamples in the biosample collection tubes of the anonymous DNA/RNA biospecimen extraction kit by the authorized lab by extracting DNA/RNA from the biosamples, sequencing the extracted DNA/RNA, encrypting resulting datasets, and depositing the encrypted resulting datasets into a unique digital repository assigned to the single shared family digital wallet, (viii) anonymously and privately notifying an authorized family member of the encrypted datasets in the unique digital repository, (ix) tokenizing the encrypted resulting datasets using a non-fungible token (for example, but not limited to, ERC1155) and storing with the shared family digital wallet, and (x) accessing the DNA/RNA datasets of the family by a family member to share, donate, process, and store as desired, wherein any transaction of the DNA/RNA datasets are recorded in a public blockchain or any Distributed Ledger Technology (DLT).

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments include an anonymous DNA/RNA donor family biospecimen tracking system and anonymous DNA/RNA donor family biospecimen tracking processes for human families using filters and non-fungible-tokens. In some embodiments, the anonymous DNA/RNA donor family biospecimen tracking system utilizes a bloom filter for members of human families to anonymously search databases and entities for indications of their anonymous DNA/RNA biospecimen being used.

In some embodiments, the anonymous DNA/RNA donor family biospecimen tracking processes include (i) an anonymous DNA/RNA donor family biospecimen preparation and ownership claiming process for human families of related donors to use an anonymous DNA/RNA biospecimen extraction kit that utilizes public key infrastructure (PKI), asymmetric encryption, and Non-Fungible-Tokens (NFT) on a public blockchain to create a self-sovereign digital DNA fingerprint for each DNA donor, relate, claim ownership, consent to use, establish biological relationship between donors, and keep track of corresponding multi-omics data sets associated with each donor biospecimen from provided in the anonymous DNA/RNA biospecimen extraction kit in some embodiments and (ii) a particular anonymous DNA/RNA biospecimen tracking process that utilizes a bloom filter for members of human families to anonymously search databases and entities for indications of their anonymous DNA/RNA biospecimen being used.

In some embodiments, the anonymous DNA/RNA donor family biospecimen preparation and ownership claiming process for human families of related donors to use an anonymous DNA/RNA biospecimen extraction kit that utilizes PKI, asymmetric encryption, and NFTs on a public blockchain to create a self-sovereign digital DNA fingerprint for each DNA donor, relate, claim ownership, consent to use, establish biological relationship between donors, and keep track of corresponding multi-omics data sets. The blockchain comprises one of a public blockchain and a distributed ledger technology blockchain. In some embodiments, the anonymous DNA/RNA donor family biospecimen preparation and ownership claiming process allows a person in the family to customize data governance by using individual or multi-signature wallets. In the end, all data is encrypted using a unique family encryption key. In some embodiments, the anonymous DNA/RNA donor family biospecimen preparation and ownership claiming process allows each member of an entire family (e.g., mother, father, children) to create a self-sovereign DNA fingerprint, using at least fifty genotyped single-nucleotide polymorphisms (SNPs), and explore the genomic revolution without risking their identities, losing track of their biosamples, corresponding datasets and customize data governance by using individual or multi signature wallets in which all data is encrypted using a unique master family encryption key. In some embodiments, the anonymous DNA/RNA donor family biospecimen preparation and ownership claiming process provides genetic/biological relationship verification that demonstrates and proves genetic familial link(s) between parent(s) and child(ren). For example, a child that is separated from one parent or both parents at a border crossing between two countries can be reunited by genetic proof linking the family together biologically/genetically. In this way, the anonymous DNA/RNA donor family biospecimen preparation and ownership claiming process results in potential minor child identification verification via familial DNA, such as from the child's biological mother and biological father. In some embodiments, the anonymous DNA/RNA donor family biospecimen preparation and ownership claiming process enhances biomedical/genetic analysis of DNA/RNA for identification of genetic mutation(s) between generations of genetically related individuals while still maintaining complete privacy of the identities of those individuals, yet ensuring that genetic/biomedical researcher or counselor knows that samples being analyzed/reviewed for mutation are genetically linked family members. In this way, tracing familial DNA mutations is made possible by the anonymous DNA/RNA biospecimen preparation and ownership claiming process because a researcher or a counselor interested in familial mutations can be assured that the biospecimen samples being analyzed/reviewed for mutation(s) are genetically linked family members (e.g., mother-child, father-child, etc.).

In some embodiments, the anonymous DNA/RNA donor family biospecimen preparation and ownership claiming process comprises (i) buying an anonymous DNA/RNA biospecimen extraction kit comprising at least three biosample collection tubes, (ii) creating a shared digital family wallet for at least three members of a family whose biosamples are to be collected in the biosample collection tubes of the anonymous DNA/RNA biospecimen extraction kit, (iii) registering the anonymous DNA/RNA biospecimen extraction kit under the shared family digital wallet, (iv) configuring a data governance scheme that requires at least one of an individual family member signature or multiple family member signatures, (v) collecting biosamples in the biosample collection tubes as provided by the members of the family, (vi) providing the anonymous DNA/RNA biospecimen extraction kit including the collected biosamples in the biosample collection tubes for delivery to an authorized lab via one of sending the anonymous DNA/RNA biospecimen extraction kit and depositing the anonymous DNA/RNA biospecimen extraction kit into an available locker slot of a local anonymous DNA/RNA biospecimen extraction kit vending machine, (vii) processing the biosamples in the biosample collection tubes of the anonymous DNA/RNA biospecimen extraction kit by the authorized lab by extracting DNA/RNA from the biosamples, sequencing the extracted DNA/RNA, encrypting resulting datasets, and depositing the encrypted resulting datasets into a unique digital repository assigned to the single shared family digital wallet, (viii) anonymously and privately notifying an authorized family member of the encrypted datasets in the unique digital repository, (ix) tokenizing the encrypted resulting datasets using a non-fungible token (for example, but not limited to, ERC1155) and storing with the shared family digital wallet, and (x) accessing the DNA/RNA datasets of the family by a family member to share, donate, process, and store as desired, wherein any transaction of the DNA/RNA datasets are recorded in a public blockchain or any Distributed Ledger Technology (DLT).

As stated above, current technology requires data sharing with a data broker that aggregates personal data of DNA biospecimen donors to the DNA/RNA datasets. This is a privacy concern for many individuals, due to the most recent data breaches and conflicts of interests with the data broker, whose sustainable business model typically involves selling user data to big pharmaceutical companies. However, the anonymous DNA/RNA biospecimen tracking process and the anonymous DNA/RNA biospecimen extraction kit described herein will enable biologically-related families (mom, dad, and children) to sequence and/or genotype their DNA/RNA for different purposes (genomic medicine, human identification, creation of a Self-sovereign Digital DNA Fingerprint for each DNA donor, proof of relationship, nutrigenomics, pharmacogenomics profile, etc.) with privacy and customizable governance of the data sets from the minors (individual digital signature or multi-signature if custody is shared among the parents or guardians of the minors). Specifically, embodiments of the anonymous DNA/RNA donor family biospecimen tracking system and anonymous DNA/RNA donor family biospecimen tracking processes for human families using filters and non-fungible-tokens described in this specification solve such problems by anonymous (private) DNA/RNA biospecimen tracking for human families by way of an anonymous DNA/RNA family biospecimen extraction kit with multiple collection tubes that families can take home to provide biosamples (saliva, swab-based, etc.) and then send back to the lab. The anonymous DNA/RNA family biospecimen extraction kit maintains family privacy and is anonymous for the biosample providers based on utilization of public key infrastructure, asymmetric encryption, and Non-Fungible-Tokens from a public Blockchain or Distributed Ledger Technology a distributed ledger to create a self-sovereign digital DNA Fingerprint for each DNA donor, relate, claim ownership, consent to use, establish biological relationship between donors, and keep track of corresponding multi-omics data sets, all without knowledge of the human personal information of the biosample providers. Specifically, the anonymous DNA/RNA family biospecimen tracking processes allow parents or guardians to buy a saliva DNA/RNA family biospecimen extraction kit that has three tubes or more (as may be needed based on the number of family members) and relate them to the same shared family digital wallet (hereinafter also interchangeably referred to as a "shared family digital wallet", "digital family wallet", "shared wallet", "single wallet", or "family wallet") that can store the private keys needed to authorize any transaction. The shared family digital wallet can be in individual or shared custody. All the transactions are recorded in a distributed ledger, e.g., a public or private blockchain, such as Ethereum. The corresponding datasets are encrypted using asymmetric encryption and tokenized as non-fungible-tokens (such as ERC1155, ERC721, ETC) referenced to the family wallet.

Embodiments of the anonymous DNA/RNA family biospecimen tracking system and processes and the anonymous DNA/RNA family biospecimen extraction kit described in this specification differ from and improve upon currently existing options. In particular, some embodiments differ by from conventional biosample genetic tracking systems of today, in which there is no method or process to privately and anonymously sequences DNA/RNA of a whole family from origin and that enables the parents or guardians in the family to have the digital governance over the corresponding datasets that are stored in an individual and distributed storage network (such as InterPlanetary File System, hereinafter referred to by the acronym "IPFS"). In contrast, the anonymous DNA/RNA family biospecimen tracking system and processes and the anonymous DNA/RNA family biospecimen extraction kit allows for governance of data ("data governance") to be configured by a family member to be able to authorize transactions as individuals or in shared custody (multi-signature required to authorize any transaction).

In addition, some embodiments of the anonymous DNA/RNA family biospecimen tracking system and processes and the anonymous DNA/RNA family biospecimen extraction kit improve upon the currently existing options because the current conventional systems or methods are not privacy-by-design products and centralize the data in a siloed database and a family loses track of the transactions done with their data, the data is also not portable and is subject to the terms and conditions imposed by the current DNA/RNA sequencing service providers. By contrast, the anonymous DNA/RNA family biospecimen tracking system and processes and the anonymous DNA/RNA biospecimen extraction kit allows entire families to explore the genomic revolution without risking their identities, losing track of their biosamples and corresponding datasets, as well as providing customized data governance by using individual or multi-signature wallets, where all data is encrypted using a unique family encryption key.

Furthermore, the anonymous DNA/RNA family biospecimen tracking system and processes of some embodiments provides genetic/biological relationship verification that demonstrates and proves genetic familial link(s) between parent(s) and child(ren). In this way, the anonymous DNA/RNA family biospecimen tracking system and processes result in potential minor child identification verification via familial DNA, such as from the child's biological mother and biological father. For example, a minor child in custody of a border agent or other authority may not possess or carry any verifiable identity documentation, making child-family pairing identifications challenging over vast spatial locations and reunification with family legally challenging, but when DNA of the child can be used to create a unique Digital Fingerprint for each DNA donor using at least 50 SNPs can be computationally linked back with the biological mother and biological father using matching algorithms whose DNA/RNA biospecimen samples have been provided through the anonymous DNA/RNA biospecimen extraction kit and tracked through a public blockchain and/or DLT.

In addition, the anonymous DNA/RNA family biospecimen tracking system and processes of some embodiments enhances biomedical/genetic analysis of DNA/RNA for identification of genetic mutation(s) between generations of genetically related individuals while still maintaining complete privacy of the identities of those individuals. In this way, tracing familial DNA mutations is made possible by the anonymous DNA/RNA family biospecimen tracking system and processes because a researcher or a counselor interested in familial mutations can be assured that the biospecimen samples being analyzed/reviewed for mutation(s) are genetically linked family members, e.g., mother-child, father-child, etc using a matching algorithm that uses at least 50 SNPs.

The anonymous DNA/RNA family biospecimen tracking system and processes and the anonymous DNA/RNA family biospecimen extraction kit of the present disclosure may be comprised of the following elements. This list of possible constituent elements is intended to be exemplary only and it is not intended that this list be used to limit the anonymous DNA/RNA family biospecimen tracking system and processes and the anonymous DNA/RNA family biospecimen extraction kit of the present application to just these elements. Persons having ordinary skill in the art relevant to the present disclosure may understand there to be equivalent elements that may be substituted within the present disclosure without changing the essential function or operation of the anonymous DNA/RNA family biospecimen tracking system and processes and the anonymous DNA/RNA family biospecimen extraction kit.

1. A family buys a kit and creates a single common (shared) digital family wallet though a website portal or DNA Test Kit Vending Machine associated with the kit (in some embodiments, a link is available on the kit materials).

2. Parents or guardians create a new shared Family Wallet and registers each kit (at least 3) under the newly created shared family wallet and configures the appropriate data governance scheme (individual signature requirement (one out of two co-signers) or multi-signature requirements (two out of two co-signers). A Master Public Address represents the Shared Family Wallet.

3. Each member of the family spits (or utilizes a swab) to obtain a biosample in a separate tube and collecting all tubes/biosamples individually and send the kit by using the pre-paid mailing service or by depositing the family kit at a local DNA vending machine available slot.

4. The authorized laboratory will process the samples, extract the DNA/RNA, sequence or genotype DNA/RNA, and deposit the corresponding datasets in the unique digital repository assigned to the corresponding digital family wallet (such as IPFS or OasisLabs Private Cloud). The data is encrypted end-to-end throughout any data transmission (sending or receiving any data) and when persisted in a decentralized database storage or distributed storage, such as IPFS or OasisLabs Cloud.

5. Parents or guardians will be notified by an alert through the private and encrypted messaging system embedded in the platform/system.

6. The datasets will be tokenized using a non-fungible-token (smart contract) such as ERC1155 and/or ERC721 and/or ERC20 and stored in the corresponding DNA/RNA digital family wallet.

7. Using at least 50 SNPs, a unique Non-fungible-token (DNA Fingerprint for each DNA donor) is created as the baseline of a Self-Sovereign Digital DNA Identity. An exemplary proposed list of SNPs includes, without limitation, the following SNPs: rs1471939, rs4666200, rs7554936, rs9530435, rs6104567, rs2272998, rs560681, rs6591147, rs321198, rs870347, rs2946788, rs4891825, rs10108270, rs2397060, rs7229946, rs13182883, rs1876482, rs315791, rs7205345, rs798443, rs4717865, rs2416791, rs2125345, rs4746136, rs13218440. rs1523537, rs1058083, rs1344870, rs7704770, rs1410059, rs5768007, rs260690, rs13400937, rs4918842, rs9809104, rs1821380, rs279844, rs952718, rs447818, rs13134862, rs4463276, rs3943253, rs6548616, rs731257, rs9319336, rs1019029, rs1358856, rs1823718, rs2503107, rs10236187, rs1513181, rs7657799, rs2504853, rs772262, rs3737576, rs445251, rs10488710, rs722869, rs1109037, rs3780962, rs7997709, rs4670767, rs9522149, rs4908343, rs12629908, rs1336071, rs740598, rs12997453, rs2352476, rs1554472, rs10007810, rs1760921, rs1040045, rs10496971, rs7803075, rs987640, rs6444724, rs10092491, rs735612, rs985492, rs9951171, rs3907047, rs1865680, rs525869, rs2040962, rs530501, rs2032624, rs1296819, rs316598, rs722290, rs1872575, rs18579, rs891700, rs8113143, rs1008730, rs17307398. This proposed list of SNPs is not an exclusive or exhaustive list, as other SNPs may be employed by the anonymous DNA/RNA family biospecimen tracking system and processes and the anonymous DNA/RNA family biospecimen extraction kit of the present disclosure.

8. The parents or guardians now can create a self-sovereign DNA Fingerprint for each DNA donor (or SSID), share, donate, process, and/or store their DNA/RNA datasets in their shared family wallet so they can interact with the service providers inside the network that has a compatible digital wallet to receive and sign a digital receipt for the corresponding datasets or token when authorized by the parents or guardian (individually or in shared custody). All of the transactions are made in peer-to-peer mode, encrypted and recorded in a public Blockchain, such as Ethereum, Bitcoin, Hadera, Tron, Oasis Labs, Hyper Ledger, and others.

The anonymous DNA/RNA family biospecimen tracking system and processes and the anonymous DNA/RNA family biospecimen extraction kit of the present disclosure is differentiated from conventional biosample collection and tracking system by the ability to anonymize all data and configure data governance using a shared blockchain based digital wallet, as well as the use of transactions that can be recorded in a public Blockchain and/or Distributed Ledger Technology, such as Ethereum or Hyper Ledger, for transparency and traceability in an encrypted peer-to-peer mode and using a shared digital family wallet. Specifically, the anonymous DNA/RNA family biospecimen tracking system and processes and the anonymous DNA/RNA family biospecimen extraction kit of the present disclosure provides customizable data governance for DNA/RNA datasets of each minor (child), such that requirements can be set for two parent signatures to be present for any and all transactions, or another customized data governance rule. Thus, either an individual signature is needed or multi-signature is required when sharing custody.

To use the anonymous DNA/RNA family biospecimen tracking system and processes and the anonymous DNA/RNA family biospecimen extraction kit of the present disclosure, one would need as many saliva/swab DNA/RNA extraction kits as the number of family members, and then create a shared family digital wallet using a portal or web page (e.g., "genobank.io") or a Saliva/Swab DNA/RNA Vending Machine, a public blockchain infrastructure to record the transactions and tokenize the data using non-fungible-tokens (smart contracts) and a sequencing (or genotyping) laboratory that agrees with privacy and digital protocol aspects. In this way, families will use the anonymous DNA/RNA family biospecimen tracking system and processes to explore genomic medicine, human identification services that require DNA/RNA, pharmacogenomic profiles, nutrigenomic services, precision food, etc., with privacy and without losing track of the chain of custody for their DNA/RNA datasets, all based on a customizable data governance scheme (individual digital signature or multi-signature requirements).

Figure 1:
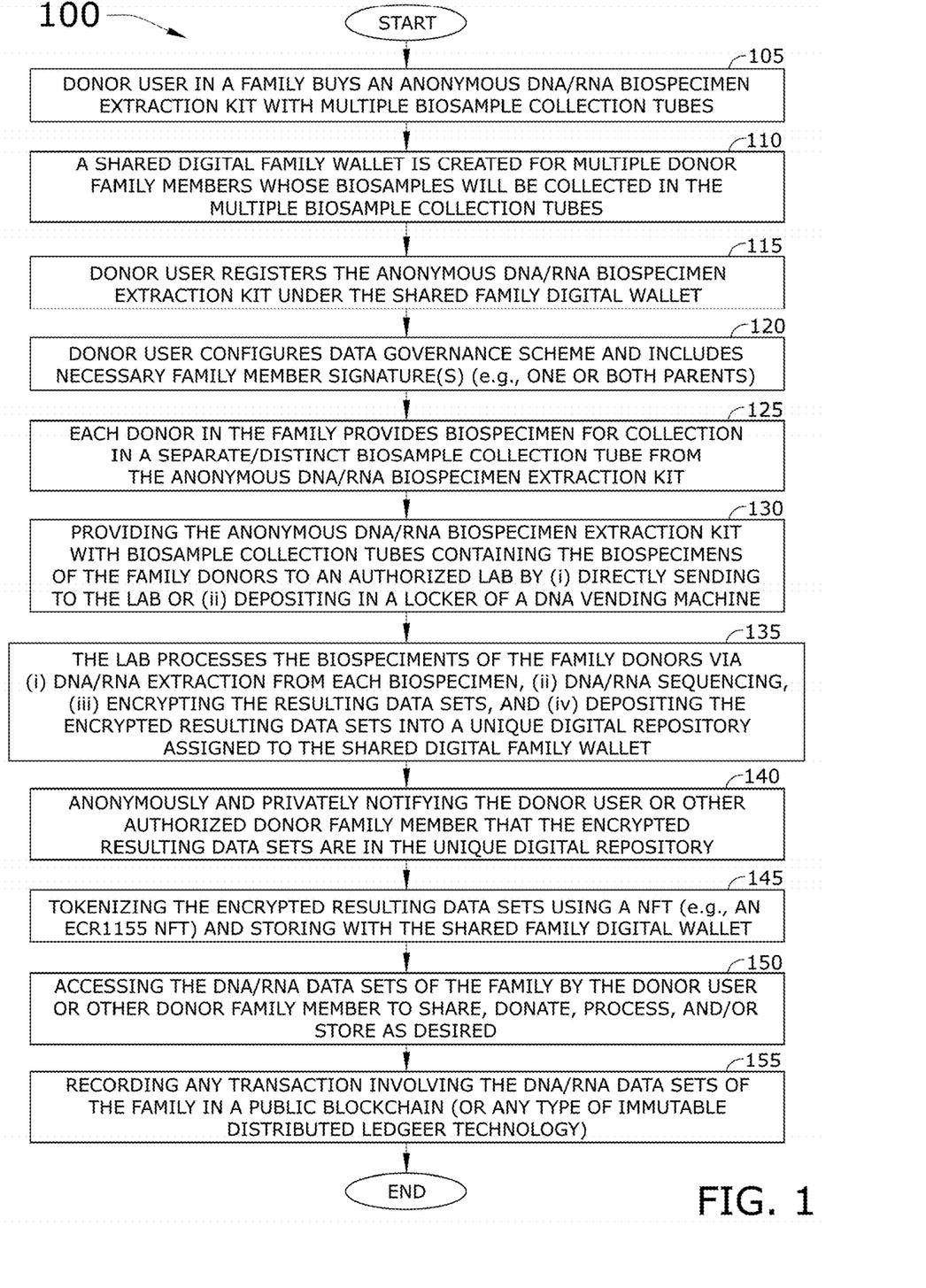
FIG. 1 conceptually illustrates an anonymous DNA/RNA donor family biospecimen preparation and ownership claiming process whereby human families of related donors use an anonymous DNA/RNA family biospecimen extraction kit that utilizes PKI, asymmetric encryption, and NFTs on a blockchain to relate, claim ownership, consent to use, establish biological relationship between donors, and keep track of corresponding multi-omics data sets associated with each donor biospecimen from provided in the anonymous DNA/RNA family biospecimen extraction kit in some embodiments.

By way of example, FIG. 1 conceptually illustrates an anonymous DNA/RNA donor family biospecimen preparation and ownership claiming process 100 whereby human families of related donors use an anonymous DNA/RNA family biospecimen extraction kit that utilizes PKI, asymmetric encryption, and NFTs on a blockchain to relate, claim ownership, consent to use, establish biological relationship between donors, and keep track of corresponding multi-omics data sets associated with each donor biospecimen from provided in the anonymous DNA/RNA family biospecimen extraction kit in some embodiments. As shown in this figure, the anonymous DNA/RNA donor family biospecimen preparation and ownership claiming process 100 starts when a donor user in a family buys or obtains an anonymous DNA/RNA family biospecimen extraction kit with multiple (three or more) biospecimen collection tubes (at 105). Next, a shared family digital wallet is created for multiple donor family members to share as a single digital wallet associated with their biospecimen samples to be collected in the multiple biosample collection tubes (at 110).

In some embodiments, the anonymous DNA/RNA donor family biospecimen preparation and ownership claiming process 100 then proceeds to the next step at which the donor user registers the anonymous DNA/RNA family biospecimen extraction kit under the shared family digital wallet that was just created (at 115). Once the shared family digital wallet is created and the donor user registers the anonymous DNA/RNA family biospecimen extraction kit under the shared family digital wallet, then the anonymous DNA/RNA donor family biospecimen preparation and ownership claiming process 100 proceeds forward to allow the donor user to configure a data governance scheme (at 120). In some embodiments, the anonymous DNA/RNA donor family biospecimen preparation and ownership claiming process 100 requires a signature from the donor user, or requires a signature from both parents in a two-parent family unit with at least one child. This requirement is followed according to governing law in a jurisdiction or by other requirement.

In some embodiments, the anonymous DNA/RNA donor family biospecimen preparation and ownership claiming process 100 moves ahead to the next step during which each donor family member individually collects a biospecimen sample in a distinct and separate collection tube from the anonymous DNA/RNA family biospecimen extraction kit (at 125). In some embodiments, the anonymous DNA/RNA donor family biospecimen preparation and ownership claiming process 100 follows with a next step during which delivery of the anonymous DNA/RNA family biospecimen extraction kit with all the collection tubes and the biospecimen samples of the family members are delivered to a sequencing lab (at 130). Specifically, the anonymous DNA/RNA donor family biospecimen preparation and ownership claiming process 100 supports deliver by any practical method including, without limitation, direct delivery by shipment or mail/package delivery to the lab and depositing the anonymous DNA/RNA family biospecimen extraction kit in a locker of a privacy-preserving biospecimen test kit kiosk and locker. Typically, a privacy-preserving biospecimen test kit kiosk and locker is a preferred, but not exclusive, delivery method when the donor user purchases or obtains the anonymous DNA/RNA family biospecimen extraction kit from the privacy-preserving biospecimen test kit kiosk and locker.

The anonymous DNA/RNA donor family biospecimen preparation and ownership claiming process 100 of some embodiments next includes a step in which the lab processes the biospecimen samples of the family donors (at 135), which includes (i) DNA/RNA extraction from each biospecimen sample, (ii) DNA/RNA sequencing, (iii) encrypting the resulting data sets, and (iv) depositing the resulting encrypted data sets in a unique digital repository assigned to the shared family digital wallet.

In some embodiments, the anonymous DNA/RNA donor family biospecimen preparation and ownership claiming process 100 then includes a step for anonymously and privately notifying the donor user (or other specified/authorized family member) that the resulting encrypted data sets are in the unique digital repository (at 140). In some embodiments, the anonymous DNA/RNA donor family biospecimen preparation and ownership claiming process 100 moves ahead to the next step for tokenizing the resulting encrypted data sets using a Non-Fungible Token (or NFT, such as an NFT under ECR1155 standard) and storing with the shared family digital wallet (at 145). In some embodiments, the anonymous DNA/RNA donor family biospecimen preparation and ownership claiming process 100 then moves forward to allow accessing of the DNA/RNA data sets of the family by the donor user or other donor family member to share, donate, process, and/or store as desired (at 150). In some embodiments, the anonymous DNA/RNA donor family biospecimen preparation and ownership claiming process 100 ensures that transactions involving the DNA/RNA data sets of the family are recorded in a public blockchain (at 155) or any other type of immutable distributed ledger technology. Then the anonymous DNA/RNA donor family biospecimen preparation and ownership claiming process 100 ends.

Figure 2:
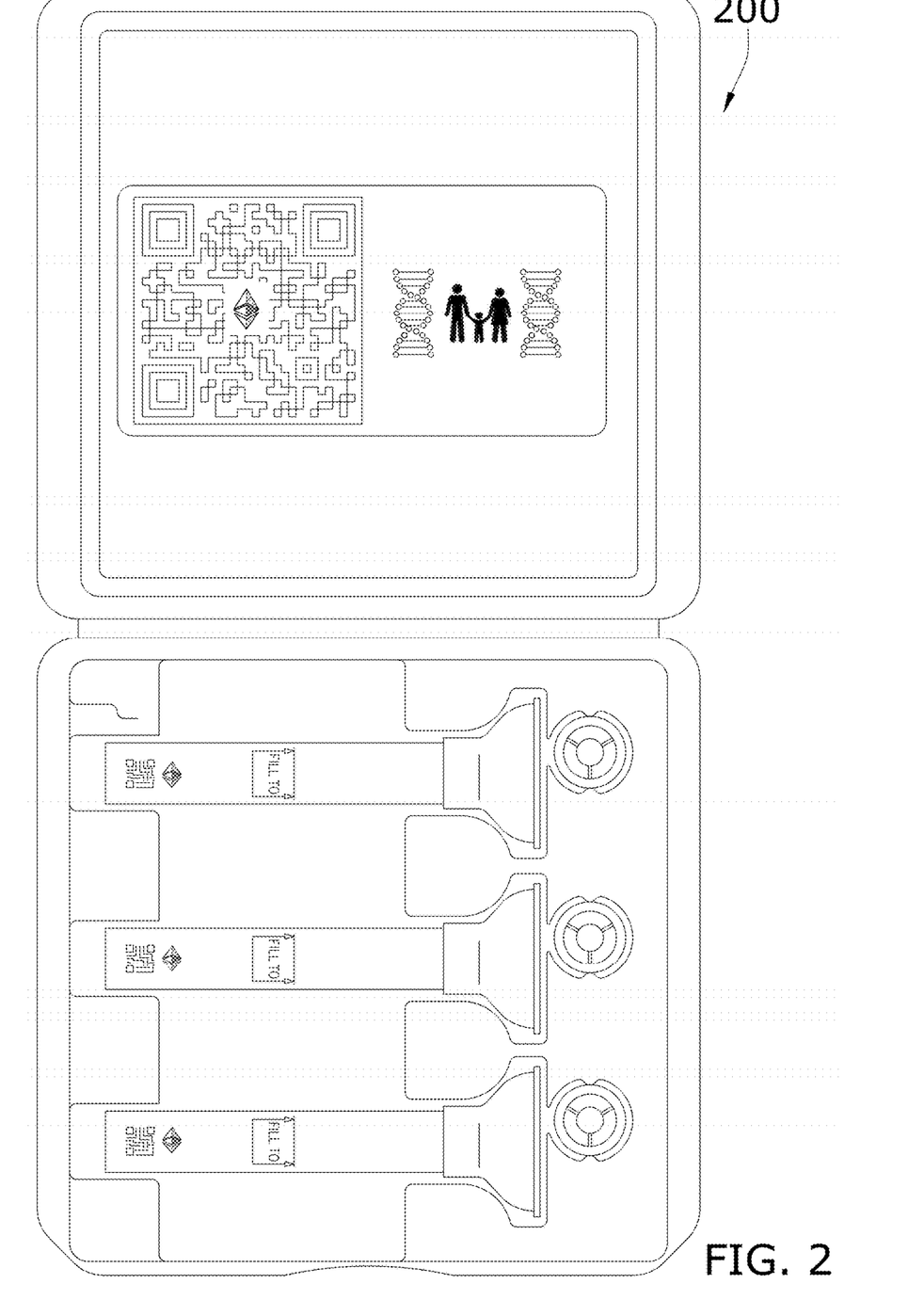
FIG. 2 conceptually illustrates an example of an anonymous DNA/RNA family biospecimen extraction kit in some embodiments for multiple family donors.

Now turning to another example, FIG. 2 conceptually illustrates an anonymous DNA/RNA donor family biospecimen extraction kit 200 in some embodiments for multiple family donors. As shown in this figure, the anonymous DNA/RNA donor family biospecimen extraction kit 200 includes three collection tubes, which would be effective for collecting biospecimen samples from a family of three members. For example, a father, a mother, and a child. Other anonymous DNA/RNA donor family biospecimen extraction kits are possible, such as those which include four collection tubes, five collection tubes, and so on. The point is to link multiple collection tubes to a family encoding, which is shown in this figure as a QR code that can be scanned by a donor user who purchases or obtains the anonymous DNA/RNA donor family biospecimen extraction kit 200. Such a "family encoding" or single extraction kit encoding can be scanned to register the extraction kit to a unique and secure shared family digital wallet. The use of a QR code for the anonymous DNA/RNA donor family biospecimen extraction kit 200 demonstrates how this occurs, as described next, by reference to FIG. 3.

Figure 3:
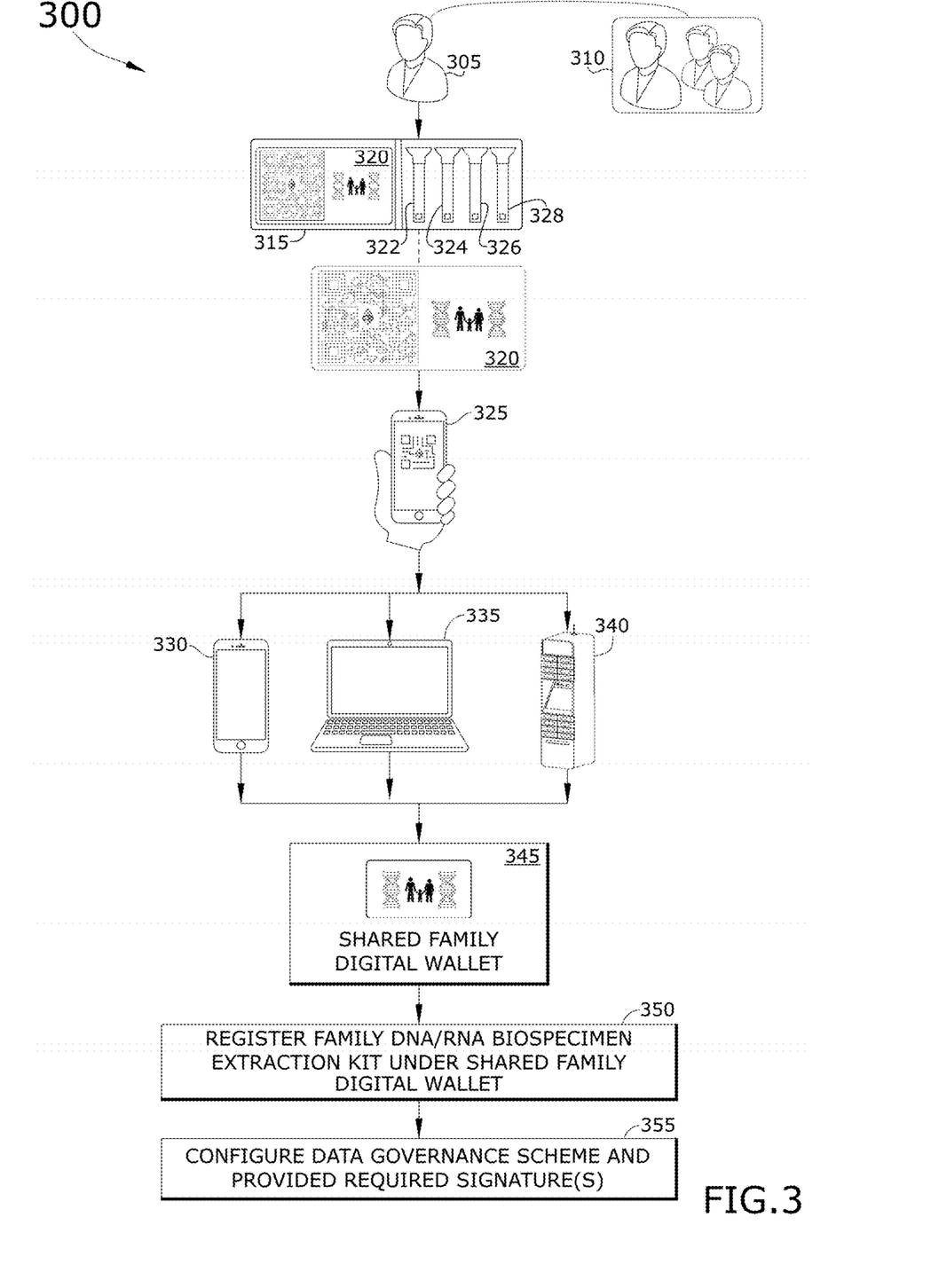
FIG. 3 conceptually illustrates a user creating a shared family digital wallet, registering an anonymous DNA/RNA family biospecimen extraction kit under the shared family digital wallet, and a configuring data governance scheme with required signatures in some embodiments.

Specifically, FIG. 3 conceptually illustrates a user creating a shared family digital wallet, registering an anonymous DNA/RNA family biospecimen extraction kit under the shared family digital wallet, and a configuring data governance scheme 300 with required signatures in some embodiments. As shown in this figure, a donor user 305 is associated with three other family members 310, and so, the donor user 305 purchases or obtains an anonymous DNA/RNA donor family biospecimen extraction kit 315 with a QR code 320 and four biospecimen collection tubes 322, 324, 326, and 328, which is enough collection tubes to collection biospecimen samples from the donor user 305 and the other three members of the family 310. The QR code 320 corresponds to the anonymous DNA/RNA donor family biospecimen extraction kit 315, and when scanned, allows the anonymous DNA/RNA donor family biospecimen extraction kit 315 to be registered with a single shared family digital wallet. In this example, the donor user 305 scans the QR code 320 with a mobile device, which shows the scanned QR code 325. In some embodiments, the QR code 320 can be scanned with other devices, such as mobile device 330, computer 335, or a privacy-preserving biospecimen test kit kiosk and locker 340. Furthermore, the donor user 305 can utilize the mobile device 330, the computer 335, and/or the privacy-preserving biospecimen test kit kiosk and locker 340 to create a shared family digital wallet 345, and then register the anonymous DNA/RNA donor family biospecimen extraction kit 315 under the shared family digital wallet 345. After creation of the shared family digital wallet 345 and registration of the anonymous DNA/RNA donor family biospecimen extraction kit 315 under the shared family digital wallet 345, the donor user 305 (and/or other members of the family 310) configures a data governance scheme 355 that applies to data sets that result from DNA/RNA sequencing and analysis performed by a lab, details of which are further described below, by reference to FIG. 4.

Figure 4:
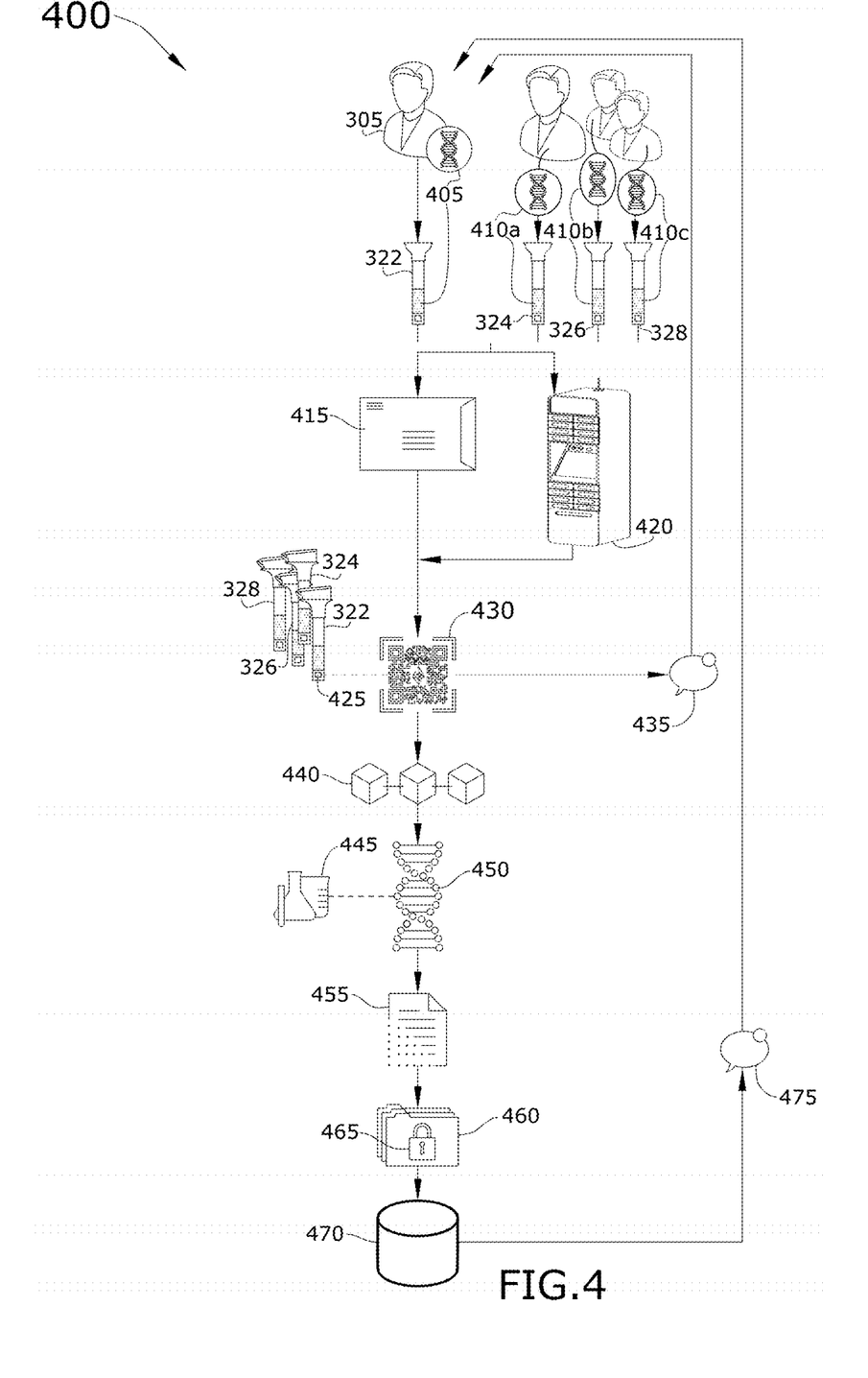
FIG. 4 conceptually illustrates a family of multiple donors collecting biospecimen samples in collection tubes of an anonymous DNA/RNA family biospecimen extraction kit, providing the collection tubes to a lab for sequencing, digitizing, and providing secure encrypted access in a data storage to the family in some embodiments.

In FIG. 4, a process 400 in which a family of multiple donors are collecting biospecimen samples in collection tubes of an anonymous DNA/RNA family biospecimen extraction kit is conceptually illustrated. The family of multiple donors includes the donor user 305 and the family members 310. The donor user 305 collects biospecimen 405 in a first collection tube 322, while the family members 310 individually and separately collect biospecimen sample 410a in a second collection tube 324, biospecimen sample 410b in a third collection tube 326, and biospecimen sample 410c in a fourth collection tube 328. The four collection tubes—namely, the first collection tube 322, the second collection tube 324, the third collection tube 326, and the fourth collection tube 328—would have been packaged together in the same anonymous DNA/RNA donor family biospecimen extraction kit, such as the anonymous DNA/RNA donor family biospecimen extraction kit 315 described above by reference to FIG. 3.

After collecting the biospecimen samples from each of the family members (including the donor user 305 and the family members 310), the anonymous DNA/RNA donor family biospecimen extraction kit is packed up and delivered to a lab for sequencing, digitizing, and providing secure encrypted access in a data storage to the family. In some embodiments, delivery to the lab includes a mail-type or shipping type delivery in which the donor user 305 or another member of the family 310 packages up the anonymous DNA/RNA donor family biospecimen extraction kit 315 with the four collection tubes containing the biospecimen samples and chooses a shipping method 415 of their own preference to deliver to the lab. On the other hand, in some embodiments, the delivery to the lab is made by way of inserting the anonymous DNA/RNA donor family biospecimen extraction kit with the four collection tubes containing the biospecimen samples into a locker of a privacy-preserving biospecimen test kit kiosk and locker 420. For example, when the donor user 305 purchases the anonymous DNA/RNA donor family biospecimen extraction kit from an integrated vending machine of a privacy-preserving biospecimen test kit kiosk and locker, then the donor user 305 or other family member 310 may be instructed to return the anonymous DNA/RNA donor family biospecimen extraction kit with the four collection tubes containing the biospecimen samples of the family.

After the lab receives the anonymous DNA/RNA donor family biospecimen extraction kit with the four collection tubes 322, 324, 326, and 328 containing the individual biospecimen samples provided by the donor user 305 and each member of the family 310, the lab scans a QR code 425 affixed to each collection tube and also the QR code of the anonymous DNA/RNA donor family biospecimen extraction kit, thereby providing a lab-scanned QR code 430. In some embodiments, the lab informs the donor user 305 or other specified member of the family 310 by way of a text message notification 435 to confirm that each collection tube 322, 324, 326, and 328 of the anonymous DNA/RNA donor family biospecimen extraction kit has been received. The lab also records the transaction on a public blockchain 440.

Next, the sequencing lab 445 extracts DNA from the biospecimen sample in each collection tube 322, 324, 326, and 328 and prepares the extracted DNA 450 of each biospecimen for digitization, as shown by digitized DNA data 455 from the sequencing process (again, for each member of the family 310, and corresponding to the DNA extracted 450 from the biospecimen sample in each collection tube 322, 324, 326, and 328). Then the digitized DNA data 455 is packaged up and secured by encryption in a data package 460 that is encrypted 465 for each individual digitized DNA data 455 corresponding to each member of the famil 310 and encrypted overall for the resulting data sets in the data package 460. In some embodiments, the encryption is secured by the donor user's private key. Next, the data package 460 as encrypted 465 is stored in a private digital repository 470, and an instructions notification message 475 with instructions for the donor user 305 or other member(s) of the family 310 to access the genomic/multiomics data in the private digital repository 470.

Figure 5:
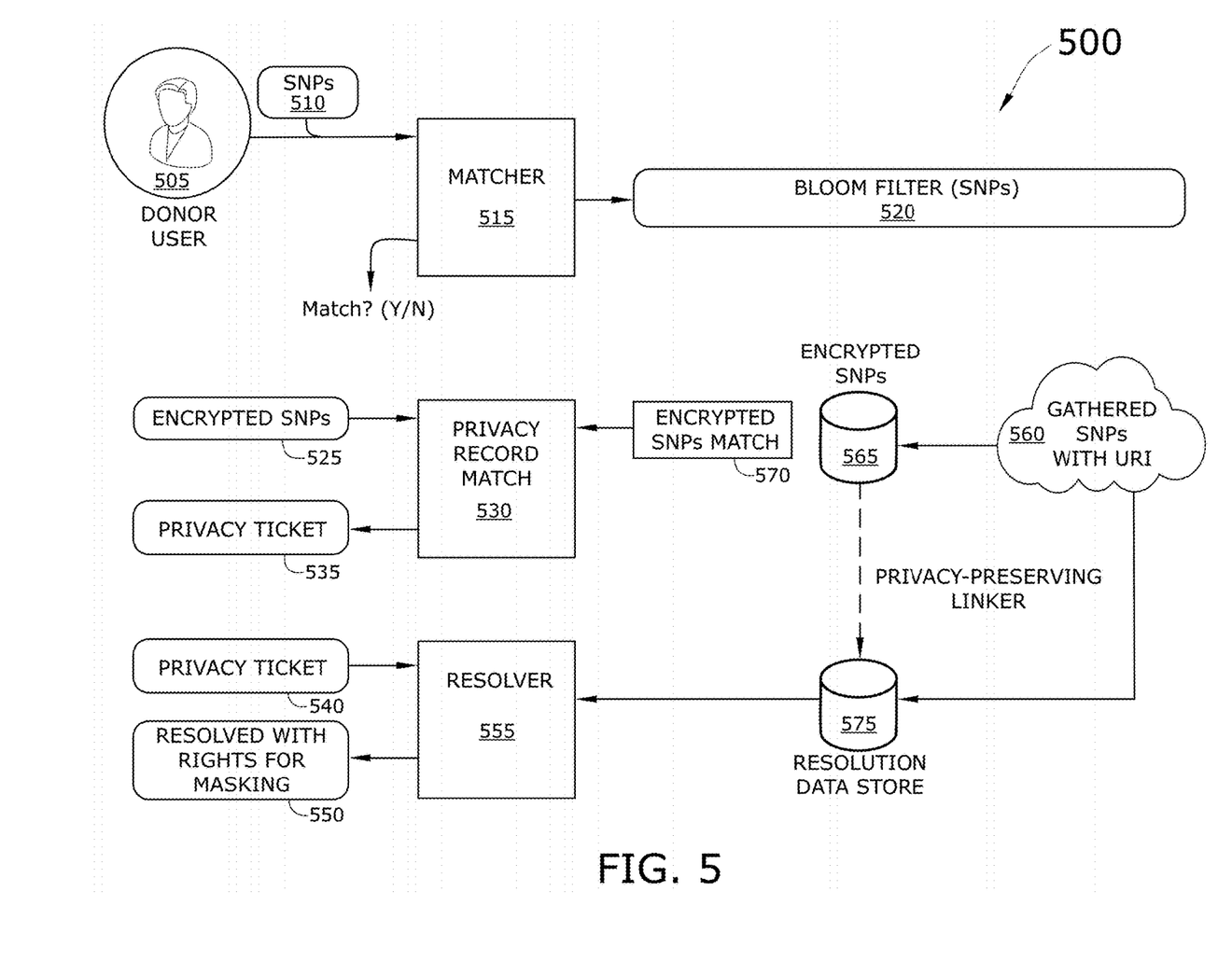
FIG. 5 conceptually illustrates a particular anonymous DNA/RNA biospecimen tracking process that utilizes a bloom filter for members of human families to anonymously search databases and entities for indications of their anonymous DNA/RNA biospecimen being used in some embodiments.

Now turning to another example, FIG. 5 conceptually illustrates a particular anonymous DNA/RNA biospecimen tracking process 500 that utilizes a bloom filter for members of human families to anonymously search databases and entities for indications of their anonymous DNA/RNA biospecimen being used in some embodiments. As shown in this figure, the particular anonymous DNA/RNA biospecimen tracking process 500 that utilizes the bloom filter demonstrates a donor user 505 with a plurality of SNPs 510 (e.g., fifty or more SNPs) which when provided to a matcher 515 process/algorithm, determines whether a search for donor user 505 identifying information is found when the SNPs 510 of the donor user 505 are searched in connection with a bloom filter 520.

Specifically, a system that utilizes a Bloom filter 520 when performing the particular anonymous DNA/RNA biospecimen tracking process 500 splits operations along two main systems (a) a matcher system 515, and (b) a resolver system 555, and includes three main stages. During a first, setup stage, the gathered SNPs 560 of the donor user 505 are encrypted and stored 565 with a unique identifier. This unique identifier is then passed to a resolution service which stores the details related to the gathered data for the SNPs. Each gathered set of SNPs 560 are split either into hash values, or split into secret shares, and then added onto a sparsely populated Bloom filter 520.

During a second, matching stage, when the donor user 505 wants to see whether his or her SNPs 510 have been registered on the system, the donor user 505 submits these and are split into hash values or shares. The Bloom filter 520 will then definitively state whether the SNPs 510 of the donor user 505 are not stored, by way of resolution data store 575. With a high probability of success, the donor user 505 will be informed if there is a successful discovery. The donor user's 505 encrypted set of SNPs 525 are then submitted to privacy record match 530 to be checked against a full set of the previously encrypted SNPs 570. A hash search will find the matches.

During a third resolving stage, the donor user 505, on one or more matches, will be delivered a privacy ticket 535 which will be used (at privacy ticket step 540) to resolve, in resolver system 555, the actual details of SNPs gathering within the resolver service 555. This includes those resolved with rights for masking 550.

Figure 6:
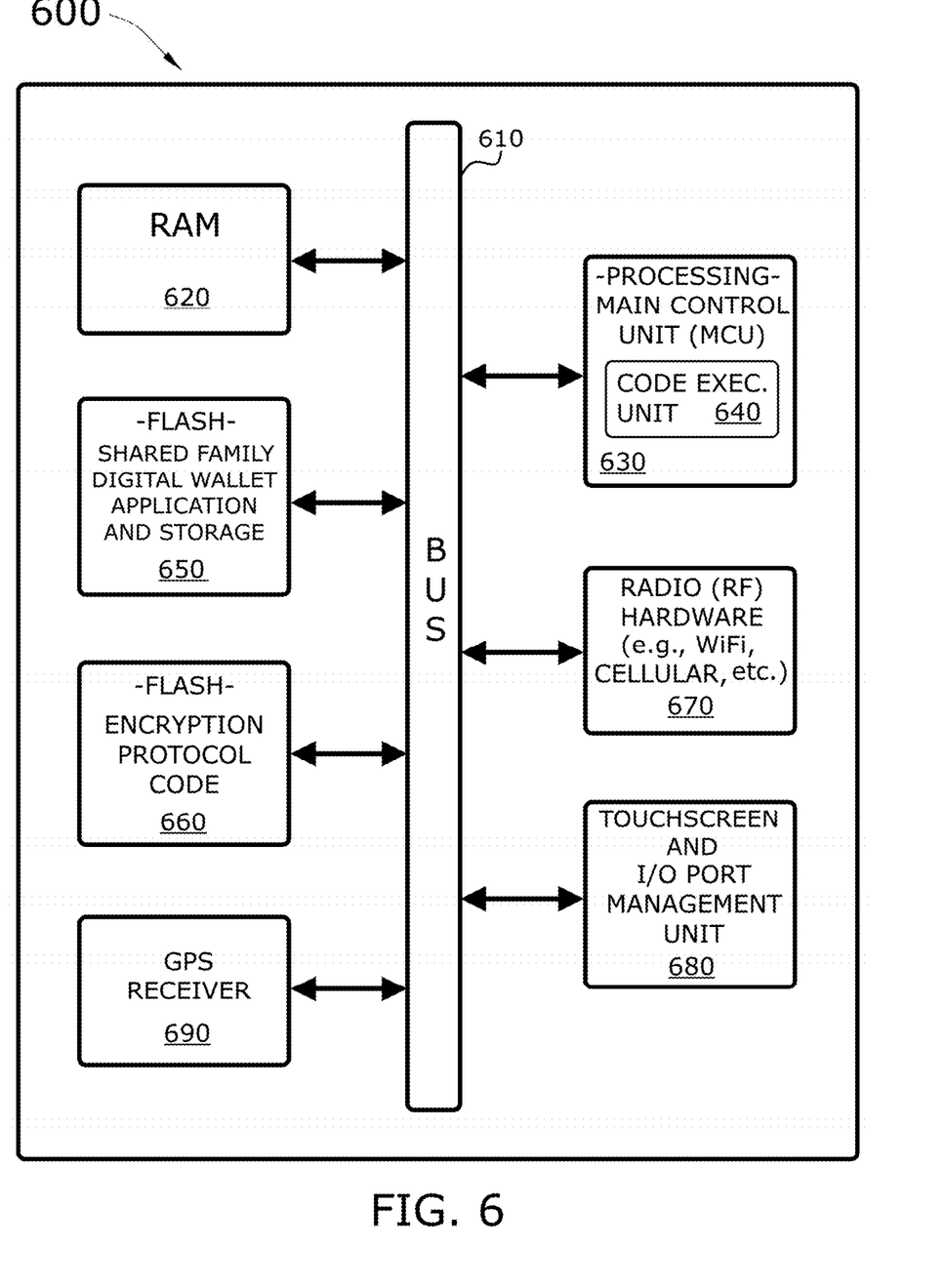
FIG. 6 conceptually illustrates a block diagram of a mobile device with a shared family digital wallet for a family of donors providing biospecimen samples in collection tubes in a privacy-preserving biospecimen test kit kiosk and locker in some embodiments.

Turning to another example, FIG. 6 conceptually illustrates a block diagram of a mobile device 600 with a shared family digital wallet for a family of donors providing biospecimen samples in collection tubes in a privacy-preserving biospecimen test kit kiosk and locker in some embodiments. As shown in this figure, the mobile device 600 includes a bus 610, a random access memory (RAM) 620, a main control unit (MCU) 630 for runtime processing to access, view, and interact with a shared family digital wallet created for the donor user and his or her family, a code execution unit 640 embedded within the MCU 630, a first persistent flash memory 650 that stores a digital wallet application and storage for the shared family digital wallet and its contents (such as non-fungible tokens, cryptocurrency, etc.), a second persistent flash memory 660 that stores encryption protocol code that is executed by code execution unit 640 of the MCU 630 to decrypt the hash encrypted data representing the post-processed biospecimen results of the user and access the contents of the shared family digital wallet by way of the digital wallet application that is stored in the first persistent flash memory 650, radio (RF) hardware 670 to transmit and receive cellular signals and other wireless data signals, a touchscreen and input/output (I/O) management unit 680, and a global positioning system (GPS) receiver 690.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the terms "software", "application", "program", "mobile app", and "app" are meant to include firmware residing in read-only memory or applications stored in magnetic storage, which can be read into memory for processing by a processor. Also, in some embodiments, multiple software inventions can be implemented as subparts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 7:
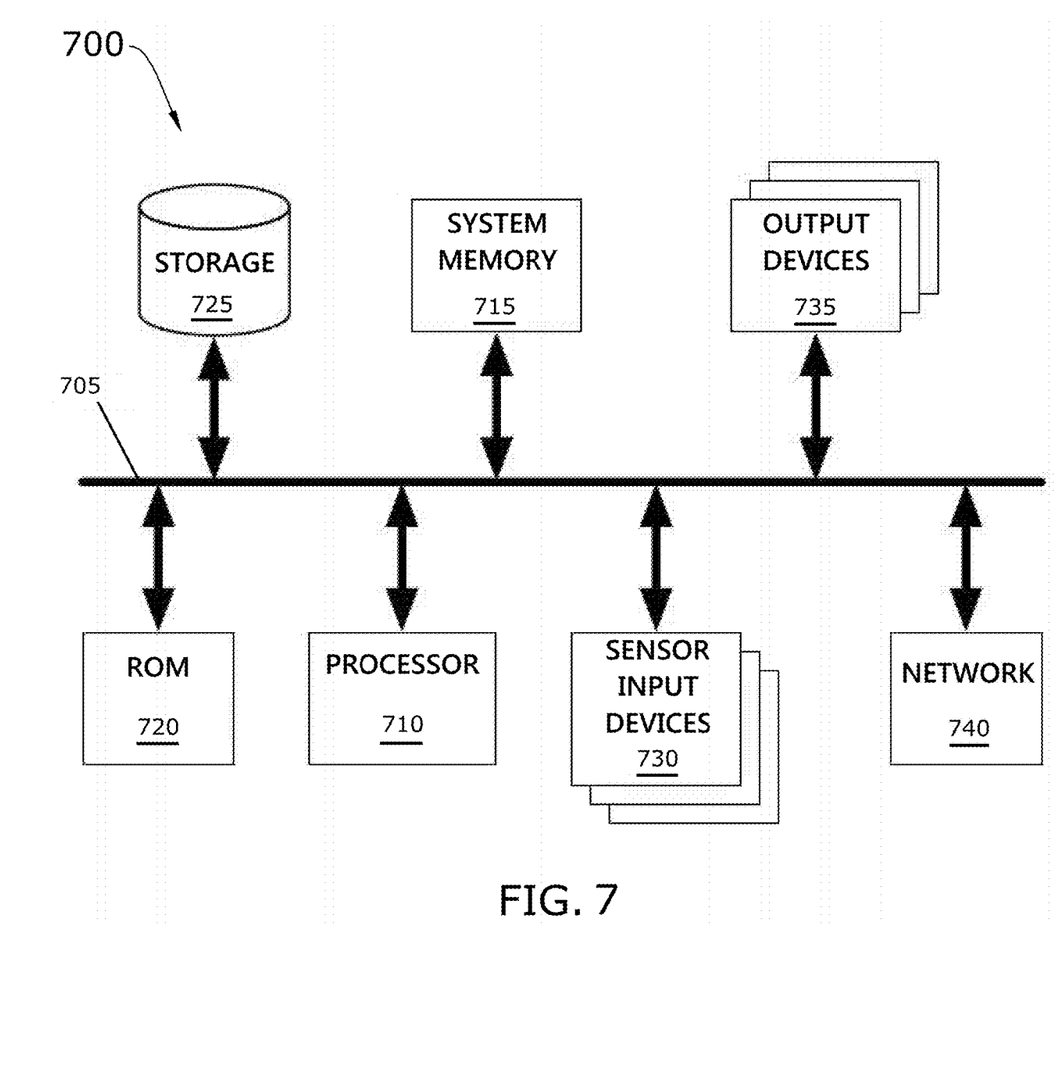
FIG. 7 conceptually illustrates an electronic system with which some embodiments of the invention are implemented.

FIG. 7 conceptually illustrates an electronic system 700 with which some embodiments of the invention are implemented. The electronic system 700 may be a computer, or any other sort of electronic computing device, such as the privacy-preserving biospecimen test kit kiosk and locker described above by reference to FIGS. 3 and 4, or the mobile device 600 described above by reference to FIG. 6. Such an electronic system 700 includes various types of computer readable media and interfaces for various other types of computer readable media. Specifically, the electronic system 700 includes a bus 705, processing unit(s) 710, a system memory 715, a read-only memory 720, a permanent storage device 725, sensor input devices 730, output devices 735, and a network 740.

The bus 705 collectively represents all system, peripheral, and chipset buses that communicatively connect the numerous internal devices of the electronic system 700. For instance, the bus 705 communicatively connects the processing unit(s) 710 with the read-only memory 720, the system memory 715, and the permanent storage device 725.

From these various memory units, the processing unit(s) 710 retrieves instructions to execute and data to process in order to execute the processes of the invention. The processing unit(s) may be a single processor or a multi-core processor in different embodiments.

The read-only-memory (ROM) 720 stores static data and instructions that are needed by the processing unit(s) 710 and other modules of the electronic system. The permanent storage device 725, on the other hand, is a read-and-write memory device. This device is a non-volatile memory unit that stores instructions and data even when the electronic system 700 is off. Some embodiments of the invention use a mass-storage device (such as a magnetic or optical disk and its corresponding disk drive) as the permanent storage device 725.

Other embodiments use a removable storage device (such as a floppy disk or a flash drive) as the permanent storage device 725. Like the permanent storage device 725, the system memory 715 is a read-and-write memory device. However, unlike storage device 725, the system memory 715 is a volatile read-and-write memory, such as a random access memory. The system memory 715 stores some of the instructions and data that the processor needs at runtime. In some embodiments, the invention's processes are stored in the system memory 715, the permanent storage device 725, and/or the read-only memory 720. For example, the various memory units include instructions for processing appearance alterations of displayable characters in accordance with some embodiments. From these various memory units, the processing unit(s) 710 retrieves instructions to execute and data to process in order to execute the processes of some embodiments.

The bus 705 also connects to the sensor input devices 730 and the output devices 735. The sensor input devices 730 capture some environmental provenance data, some user-specific bodily information that provides pseudo-anonymous identification data for creation of a personal digital wallet by the electronic system 700, and detect other information in and around each installed privacy-preserving biospecimen test kit kiosk and locker. The sensor input devices 730 include a weight scale, a height sensor, an air quality sensor, a global positioning system (GPS) sensor, a humidity sensor, a temperature sensor, and internal locker detection sensors. In some embodiments, one or more of the internal locker detection sensors is an infrared (IR) sensor. In some embodiments, the sensor input devices 730 further include non-sensory, information capturing devices including a camera and a microphone. In some embodiments, one or more of the internal locker detection sensors is a camera. The output devices 735 display images, textual information, and other graphical information generated by the electronic system 700. The output devices 735 include printers, such as a printer that is embedded within the privacy-preserving biospecimen test kit kiosk and locker described above by reference to Figured 3 and 4. The output devices 735 also include display devices. In some embodiments, the output display devices 735 include a touchscreen, which functions as both an input and output device.

Finally, as shown in FIG. 7, bus 705 also couples electronic system 700 to a network 740 through a network adapter (not shown) or a cellular antenna, such as the cellular antenna 126 described above, by reference to FIG. 1. In this manner, the computer can be a part of a network of computers (such as a local area network ("LAN"), a wide area network ("WAN"), or an intranet), a network of networks (such as the Internet), or a cellular network. Any or all components of electronic system 700 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

We claim:

1. An anonymous DNA/RNA biospecimen tracking process for human families to use an anonymous DNA/RNA biospecimen extraction kit that utilizes public key infrastructure, asymmetric encryption, and Non-Fungible-Tokens from a public Blockchain or Distributed Ledger Technology blockchain to create a Self-Sovereign Digital DNA Fingerprint for each DNA donor, relate, claim ownership, consent to use, establish biological relationship between donors, and keep track of corresponding multi-omics data sets, the anonymous DNA/RNA biospecimen tracking process comprising:

buying an anonymous DNA/RNA biospecimen extraction kit comprising at least three biosample collection tubes;

creating a shared digital family wallet for at least three members of a family whose biosamples are to be collected in the biosample collection tubes of the anonymous DNA/RNA biospecimen extraction kit;

registering the anonymous DNA/RNA biospecimen extraction kit under the shared family digital wallet;

configuring a data governance scheme that requires at least one of an individual family member signature and multiple family member signatures;

collecting biosamples in the biosample collection tubes as provided by the members of the family;

providing the anonymous DNA/RNA biospecimen extraction kit for delivery to an authorized lab, said anonymous DNA/RNA biospecimen extraction kit including the collected biosamples in the biosample collection tubes, wherein providing the anonymous DNA/RNA biospecimen extraction kit comprises one of sending the anonymous DNA/RNA biospecimen extraction kit and depositing the anonymous DNA/RNA biospecimen extraction kit into an available slot of a local DNA vending machine;

processing the biosamples in the biosample collection tubes of the anonymous DNA/RNA biospecimen extraction kit by the authorized lab, wherein processing the biosamples comprises extracting DNA/RNA from the biosamples, sequencing or genotyping the extracted DNA/RNA, encrypting resulting datasets, and depositing the encrypted resulting datasets into a unique digital repository assigned to the single family digital wallet;

anonymously and privately notifying an authorized family member of the encrypted datasets in the unique digital repository;

tokenizing the encrypted resulting datasets using a non-fungible token and storing with the shared family digital wallet;

creating a unique Self-Sovereign digital DNA Fingerprint for each donor using at least fifty single-nucleotide polymorphisms (SNPs);

utilizing a bloom filter for the members of the family to anonymously search for indications of usage of the DNA/RNA from the biosamples; and accessing the DNA/RNA datasets of the family by a family member to share, donate, process, and store as desired, wherein any transaction of the DNA/RNA datasets is recorded in a distributed public ledge blockchain.

2. The anonymous DNA/RNA biospecimen tracking process of claim 1, wherein utilizing a bloom filter comprises:

providing the SNPs of a particular donor member of the family to a matcher system; and determining whether identifying information of the particular donor member of the family is found during a search for the SNPs of the particular donor member of the family in connection with the bloom filter.

3. The anonymous DNA/RNA biospecimen tracking process of claim 1, wherein creating the unique Self-Sovereign digital DNA Fingerprint for each donor comprises:

gathering, by a matcher system, the SNPs for the donor;

encrypting and storing, by the matcher system, the gathered SNPs with the unique Self-Sovereign digital DNA Fingerprint for the donor.

4. The anonymous DNA/RNA biospecimen tracking process of claim 3, wherein creating the unique Self-Sovereign digital DNA Fingerprint for each donor further comprises:

passing, by the matcher system, the unique Self-Sovereign digital DNA Fingerprint for the donor to a resolution service;

storing, by the resolution service, details of data related to the gathered SNPs for the donor;

splitting, by the resolution service, the gathered SNPs for the donor; and adding the split SNPs onto the bloom filter.

5. The anonymous DNA/RNA biospecimen tracking process of claim 4, wherein splitting the gathered SNPs for the donor comprises splitting the gathered SNPs into separate hash values.

6. The anonymous DNA/RNA biospecimen tracking process of claim 4, wherein splitting the gathered SNPs for the donor comprises splitting the gathered SNPs into secret shares.

* * * * *